US010961533B2

(12) United States Patent
Yoo et al.

(10) Patent No.: US 10,961,533 B2
(45) Date of Patent: Mar. 30, 2021

(54) STEM CELL WITH SUPPRESSED SOCS AND IMPROVED IMMUNOSUPPRESSIVE ABILITY AND USE THEREOF (71) Applicant: CELLnLIFE Inc., Seoul (KR)

(72) Inventors: Keon Hee Yoo, Seoul (KR); Hong Hoe Koo, Seoul (KR); Myoung Woo Lee, Seoul (KR); Dae Seong Kim, Gyeonggi-do (KR)

(73) Assignee: CELLNLIFE INC., Seoul (KR)

( * ) Notice: Subject to any disclaimer, the term of this patent is extended or adjusted under 35 U.S.C. 154(b) by 130 days.

(21) Appl. No.: 15/774,241

(22) PCT Filed: Oct. 31, 2016

(86) PCT No.: PCT/KR2016/012342
§ 371 (c)(1),
(2) Date: May 7, 2018

(87) PCT Pub. No.: WO2017/082562
PCT Pub. Date: May 18, 2017

(65) Prior Publication Data
US 2018/0320178 A1 Nov. 8, 2018

(30) Foreign Application Priority Data

Nov. 9, 2015 (KR) .................. 10-2015-0156594
Oct. 27, 2016 (KR) .................. 10-2016-0140756

(51) Int. Cl.
*C12N 15/113* (2010.01)
*A61K 35/28* (2015.01)
*C12N 5/0775* (2010.01)
*A61K 35/50* (2015.01)
*A61K 35/34* (2015.01)
*A61K 35/35* (2015.01)
*A61K 35/51* (2015.01)
*A61K 35/30* (2015.01)
*A61P 37/06* (2006.01)
*A61K 35/12* (2015.01)

(52) U.S. Cl.
CPC ............ *C12N 15/113* (2013.01); *A61K 35/28* (2013.01); *A61K 35/30* (2013.01); *A61K 35/34* (2013.01); *A61K 35/35* (2013.01); *A61K 35/50* (2013.01); *A61K 35/51* (2013.01); *A61P 37/06* (2018.01); *C12N 5/0662* (2013.01); *C12N 5/0667* (2013.01); *A61K 2035/122* (2013.01); *C12N 2310/111* (2013.01); *C12N 2310/122* (2013.01); *C12N 2310/14* (2013.01); *C12N 2310/141* (2013.01); *C12N 2310/531* (2013.01); *C12N 2501/24* (2013.01); *C12N 2501/65* (2013.01); *C12N 2501/998* (2013.01)

(58) Field of Classification Search
CPC .................................................. C12N 15/113
See application file for complete search history.

(56) References Cited

FOREIGN PATENT DOCUMENTS

| CN | 103898050 A | 7/2014 | |
|---|---|---|---|
| JP | 2010-159215 A | 7/2010 | |
| JP | 2018-061525 A | 4/2018 | |
| KR | 2014-0128623 A | 11/2014 | |
| WO | WO-2012-112079 A1 | 8/2012 | |
| WO | WO-2014-201021 A2 | 12/2014 | |
| WO | WO-2015-084897 A2 | 6/2015 | |
| WO | WO-2015084897 A2 * | 6/2015 | ......... C12N 15/1138 |

OTHER PUBLICATIONS

Corning Catalog (Year: 2012).*
Office Action from corresponding Japanese Patent Application No. 2018-523505, dated Feb. 26, 2019.
Zhang, L., et al.; "SOCS1 Regulates the Immune Modulatory Properties of Mesenchymal Stem Cells by Inhibiting Nitric Oxide Production", PLOS One, 2014, vol. 9, Issue 5, pp. 1-9.
Sivanathan, K. N., et al.; "Interferon-Gamma Modification of Mesenchymal Stem Cells: Implications of Autologous and Allogeneic Mesenchymal Stem Cell Therapy in Allotransplantation", Stem Cell Reviews and Reports, 2014, vol. 10, pp. 351-375.
Lee, M. W., et al.; "Effect of Ex Vivo Culture Conditions on Immunosuppression by Human Mesenchymal Stem Cells", Research Article, BioMed Research International, 2013, Article ID 154919, pp. 1-11.
Office Action from corresponding Japanese Patent Application No. 2018-523505, dated Jul. 16, 2019.
Ling, W., et al., (2014) "Mesenchymal Stem Cells Employ IDO to Regulate Immunity in Tumor Microenvironment.", Cancer Res., 74(5):1576-1587, (Mar. 1, 2014).
Mbongue, J. C., et al., (2015) "The Role of Indoleamine 2, 3-Di xygenase in Immune Suppression and Autoimmunity.", Vanccines, 3:703-729, (Sep. 10, 2015).

(Continued)

Primary Examiner — Thaian N. Ton
Assistant Examiner — David A. Montanari
(74) Attorney, Agent, or Firm — Harness, Dickey & Pierce, P.L.C.

(57) ABSTRACT

The present invention relates to a stem cell having an immunosuppressive ability in which the expression or activity of a suppressor of cytokine signaling (SOCS) is inhibited, and a pharmaceutical composition for inhibiting immunity, which includes the stem cell. In addition, the present invention relates to a composition for inducing the immunosuppressive activity of a stem cell, including a suppressor of cytokine signaling (SOCS) expression or activity inhibitor. The inhibition of suppressor of cytokine signaling (SOCS) expression or activity, according to the present invention, may enhance the immunosuppressive ability of a stem cell, and the stem cell with enhanced immunosuppressive ability may be used as an effective cell therapeutic agent in an autoimmune disease, rejection upon organ transplantation, or an allergic disease.

4 Claims, 8 Drawing Sheets (56) References Cited

OTHER PUBLICATIONS

Shi, Y., et al., (2010) "Mesenchymal stem cells: a new strategy for immunosuppression and tissue repair.", *Cell Res.*, 20:510-518, (Apr. 6, 2010).

Office Action from corresponding Korean Patent Application No. 10-2016-0140756, dated May 24, 2018.

Zhang, L., et al.: "SOCS1 Regulates the Immune Modulatory Properties of Mesenchymal Stem Cells by Inhibiting Nitric Oxide Production", PLOS One, www.plosone.org, May 2014, vol. 9, Issue 5, e97256, pp. 1-9.

Philip, et al. (2015) "Stress-Immune-Growth Interactions: Cortisol Modulates Suppressors of Cytokine Signaling and JAK/STAT Pathway in Rainbow Trout Liver." *PLOS One.* 10(6):1-18 (Jun. 17, 2015) DOI :10.1371/journal.pone.0129299.

International Search Report dated Jan. 31, 2017 in International Patent Application No. PCT/KR2016/012342, with English Translation.

* cited by examiner

STEM CELL WITH SUPPRESSED SOCS AND IMPROVED IMMUNOSUPPRESSIVE ABILITY AND USE THEREOF

CROSS-REFERENCE TO RELATED APPLICATIONS

This application is a national phase application of PCT Application No. PCT/KR2016/012342, filed on 30 Jun. 2016, which claims priority to Korean Patent Application No. 10-2015-0156594, filed on 9 Nov. 2015 and Korean Patent Application No. 10-2016-0140756, filed on 27 Oct. 2016. The entire disclosures of the applications identified in this paragraph is incorporated herein by reference.

FIELD

The present invention relates to stem cells having an immunosuppressive ability in which the expression or activity of a suppressor of cytokine signaling (SOCS) is inhibited, and a pharmaceutical composition for inhibiting immunity, which includes the stem cells.

In addition, the present invention relates to a composition for inducing the immunosuppressive activity of stem cells, including a suppressor of cytokine signaling (SOCS) expression or activity inhibitor.

In addition, the present invention relates to a method of inducing the immunosuppressive activity of stem cells through the inhibition of SOCS expression or activity.

BACKGROUND

Organ, tissue or cell transplantation can be used to save the lives of patients suffering from a wide variety of diseases. Allotransplantation of human organs such as the kidneys, the liver, the heart, the lungs, and the pancreas, human tissues such as skin, and human cells such as bone marrow is a method of treating intractable diseases such as terminal organ failure, and is already used generally in hospital. In addition, xenotransplantation using mammals except for humans as donors, which is a method that can be substituted due to a lack of allotransplantation donors, has been actively researched. In particular, transplantation of stem cells capable of permanently regenerating themselves and differentiating into various types of cells constituting the body under appropriate conditions has recently emerged as one of the cell replacement therapies for various intractable diseases.

Generally, the immune system of a recipient, which normally functions, recognizes the transplanted organ, tissue or cells as "non-self," thus inducing an immune rejection response to a graft. This immune rejection response is generally mediated by alloreactive or xenoreactive T cells present in a recipient's immune system that recognizes alloantigens or xenoantigens of donor tissues. Thus, for the long-term survival of allografts or xenografts, they should be able to avoid a recipient's immune system that recognizes a foreign antigen or suppress the immune response. To avoid a recipient's immune response to a graft, immunosuppressants are generally administered to recipients. Representative examples of immunosuppressants include, but are not limited to, calcineurin inhibitors such as cyclosporin and tacrolimus (FK-506), and antiproliferative drugs such as azathioprine, rapamycin, mycophenolate mofetil, and cyclophosphamide, and these immunosuppressants are currently used frequently in allotransplantation of the kidneys, the liver, the pancreas, and the heart.

These immunosuppressants should be administered on a daily basis, and when administration thereof is stopped, an immune rejection response is generally caused. Therefore, these immunosuppressants should be administered over a long period of time, which may lead to toxic nephrosis, hepatotoxicity, or hypertension. In addition, these drugs are not specific immunosuppressants that selectively act only on immune cells responding only to alloantigens of a graft, and thus may cause side effects such as opportunistic infections due to nonspecific immunosuppression or tumor formation such as lymphomas. As another immunosuppression method, there is a method of administering a monoclonal antibody such as OKT3, daclizumab, or basiliximab, but these monoclonal antibodies are non-specific immunosuppressants and have problems such as opportunistic infections or tumor formation. Therefore, there is a need to develop a novel immunosuppression method that does not have problems such as drug toxicity, opportunistic infections, or the like.

Meanwhile, human mesenchymal stem cells (MSCs) may be derived from various tissues, and are strong candidates for cell-based transplantation or regenerative medicine treatment.

Characteristics of MSCs such as migration to damaged tissues, immunosuppressive function, self-renewal, and multipotency open up the possibility of therapeutic application thereof. Currently, about 500 clinical trials including injection or transplantation of MSCs are registered in ClinicalTrials.gov. In addition, about 20% of the clinical trials are associated with the immunosuppressive ability of MSCs. Although immunosuppressive properties of MSCs have been discovered and most phase 1 clinical trials do not exhibit biological stability problems, further clinical trials have yielded poor results.

Furthermore, since there is no culture method or protocol for standardization of MSCs, phenotypic and functional diversity has also been observed also in the case of MSCs isolated from the same tissue of the same recipient. Therefore, there is a need for a method of promoting or inhibiting the function of MSCs by imparting specific conditions.

DETAILED DESCRIPTION

Technical Problem

As a result of having made intensive efforts to develop a method of enhancing an immunosuppressive ability of stem cells, the inventors of the present invention verified that the inhibition of SOCS expression in stem cells could enhance the immunosuppressive ability of stem cells, thus completing the present invention.

Therefore, an object of the present invention is to provide a stem cell having an immunosuppressive ability in which the expression or activity of a suppressor of cytokine signaling (SOCS) is suppressed, and a pharmaceutical composition for inhibiting immunity, which includes the stem cell.

In addition, another object of the present invention is to provide a composition for inducing the immunosuppressive activity of a stem cell, which includes a suppressor of cytokine signaling (SOCS) expression or activity inhibitor.

In addition, still another object of the present invention is to provide a method of inducing the immunosuppressive activity of a stem cell through the inhibition of suppressor of cytokine signaling (SOCS) expression or activity.

Technical Solution

An embodiment of the present invention provides a stem cell having an immunosuppressive ability in which the expression or activity of a suppressor of cytokine signaling is suppressed.

Hereinafter, the present invention will be described in detail.

In the present invention, a suppressor of cytokine signaling (SOCS) protein belongs to the negative feedback regulator group of cytokine signaling, and is known to include Janus kinase/signal transducer and activators of the JAK/STAT pathway. In addition, according to a recent report, SOCS proteins are capable of acting as negative regulators of the signaling of receptor tyrosine kinase (RTKs) including insulin receptors (IRs), epithelial growth factor receptor (EGFR), and KIT.

The type of SOCS is not limited, and examples of the SOCS include cytokine-inducible SH2-containing protein (CISH), SOCS1, SOCS2, SOCS3, SOCS4, SOCS5, SOCS6, and SOCS7. In addition, most preferably, the SOCS may be SOCS1 or SOCS3.

The term "stem cell" as used herein refers to an undifferentiated cell that has the ability to differentiate into various body tissues, and these stem cells may be classified as totipotent stem cells, pluripotent stem cells, and multipotent stem cells.

In the present invention, the stem cell may be an embryonic stem cell, a mesenchymal stem cell, a cancer stem cell, or an induced pluripotent stem cell, depending on the origin or type thereof.

In addition, the term "mesenchymal stem cell (MSC)" as used herein refers to a multipotent stem cell that has the ability to differentiate into various mesodermal cells including bone, cartilage, adipocytes, and muscle cells or ectodermal cells such as nerve cells. The mesenchymal stem cell may be preferably derived from one selected from the group consisting of umbilical cord, umbilical cord blood, bone marrow, fat, muscle, nerves, skin, amniotic membranes, chorionic membranes, decidual membranes, and placentas. In addition, the mesenchymal stem cell may be derived from a human, an embryo, or a mammal except for a human. The mammal except for a human may be more preferably a canine animal, a feline animal, a monkey, a cow, sheep, a pig, a horse, a rat, a mouse, a guinea pig, or the like, and the origin is not limited.

In a specific embodiment of the present invention, to increase the immunosuppressive ability of mesenchymal stem cells, SOCS1 or SOCS3 down-regulated MSCs were prepared using siRNA and shRNA for inhibiting SOCS expression. Subsequently, it was confirmed that the SOCS down-regulated MSCs not only inhibited T-cell proliferation in vitro, but also suppressed immunity and thus increased a survival rate in an in vivo graft-versus-host disease animal model.

Accordingly, the present invention provides a composition for inducing the immunosuppressive activity of a stem cell, which includes a suppressor of cytokine signaling (SOCS) expression or activity inhibitor.

The suppressor of cytokine signaling (SOCS) expression inhibitor may be an antisense nucleotide, small hairpin RNA (shRNA), small interfering RNA (siRNA), peptide nucleic acids (PNAs), DNAzymes, or ribozymes that complementarily binds to mRNA encoding the suppressor of cytokine signaling (SOCS).

In addition, the SOCS activity inhibitor may be a compound, peptide, peptidomimetic, substrate analogue, aptamer, antibody, or an SOCS antagonist that specifically binds to the SOCS, or other extracts or compounds that exhibit the SOCS inhibitory activity.

In addition, the present invention provides a composition for inhibiting immunity, which includes, as an active ingredient, the stem cell having an immunosuppressive ability in which the expression or activity of a suppressor of cytokine signaling (SOCS) is suppressed.

The composition may be intended for the prevention or treatment of humoral rejection, a graft-versus-host disease, rejection upon organ transplantation, an autoimmune disease, or an allergic disease.

The type of autoimmune disease is not limited, but may be Crohn's disease, erythema, atopy, rheumatoid arthritis, Hashimoto's thyroiditis, malignant anemia, Edison's disease, type 1 diabetes, lupus, chronic fatigue syndrome, fibromyalgia, hypothyroidism, hyperthyroidism, scleroderma, Behcet's disease, inflammatory bowel disease, multiple sclerosis, myasthenia gravis, Meniere's disease, Guilian-Barre syndrome, Sjogren's syndrome, leukoplakia, endometriosis, psoriasis, systemic scleroderma, asthma, or ulcerative colitis.

In addition, the allergic disease may be anaphylaxis, allergic rhinitis, asthma, allergic conjunctivitis, allergic dermatitis, atopic dermatitis, contact dermatitis, urticaria, pruritus, insect allergies, food allergies, or drug allergies.

The active ingredient includes a stem cell culture solution including the stem cell, a concentrate of the culture, or the like.

When the composition is prepared as a pharmaceutical composition for inhibiting immunity, the composition may include a pharmaceutically acceptable carrier. The pharmaceutically acceptable carrier, which is commonly used in formulation, may be lactose, dextrose, sucrose, sorbitol, mannitol, starch, acacia gum, calcium phosphate, alginates, gelatin, calcium silicate, micro-crystalline cellulose, polyvinylpyrrolidone, cellulose, water, syrup, methyl cellulose, methylhydroxy benzoate, propylhydroxy benzoate, talc, magnesium stearate, or mineral oil, but the present invention is not limited to the above examples. The pharmaceutical composition may further include, in addition to the above-described components, a lubricant, a wetting agent, a sweetener, a flavor enhancer, an emulsifying agent, a suspension agent, a preservative, or the like.

The pharmaceutical composition for inhibiting immunity may be orally or parenterally administered. Non-limiting examples of parenteral administration include intravenous injection, subcutaneous injection, muscle injection, intraperitoneal injection, endothelial administration, topical administration, intranasal administration, intrapulmonary administration, and intrarectal administration. Upon oral administration, since proteins or peptides are digested, an oral composition should be formulated such that an active drug is coated or protected from digestion in the stomach. In addition, the composition may be administered by an arbitrary device capable of delivering the active ingredient to a target cell.

A suitable dose of the pharmaceutical composition for inhibiting immunity may be variously prescribed according to factors such as formulation method, administration method, the age, body weight, gender, and pathological conditions of patients, diet, administration time, administration route, excretion speed, and reaction sensitivity. A suitable dosage of the composition ranges from 100 (102) cells/kg to 100,000,000 (108) cells/kg for an adult. The term "pharmaceutically effective amount" as used herein refers to an amount sufficient to prevent or treat cancer or a disease caused by angiogenesis.

The composition may be formulated using a pharmaceutically acceptable carrier and/or an additive according to a method that may be easily carried out by one of ordinary skill in the art to be prepared in a unit dose form or to be contained in a multi-dose container. In this regard, the formulation may be a solution in oil or an aqueous medium, a suspension, a syrup, an emulsifying solution, an extract, powder, granules, a tablet, or a capsule, and may further include a dispersing or stabilizing agent. In addition, the composition may be administered as an individual therapeutic agent or in combination with other therapeutic agents, and may be consecutively or simultaneously administered along with a conventional therapeutic agent. In addition, the composition may be administered once or additionally administered as needed.

In addition, another embodiment of the present invention provides a method of inducing the immunosuppressive activity of a stem cell, including inhibiting the expression or activity of a suppressor of cytokine signaling (SOCS) in the stem cell.

The inhibition of suppressor of cytokine signaling (SOCS) expression or activity may be performed by an SOCS expression or activity inhibitor, and definition thereof is the same as described above.

In addition, the stem cell may be further treated with interferon gamma (IFN-γ).

As described above, upon treatment with interferon gamma in a cell culturing process, in the stem cell, the expression of HLA-DRA (major histocompatibility complex, class II, DR alpha chain), CD274 (B7H1, B7 homolog 1), indoleamine 2,3-dioxygenase (IDO), intercellular adhesion molecule 2 (ICAM2), chemokine (C-C motif) ligand 8 (CCL8), chemokine (C-X-C motif) ligand 9 (CXCL9), or chemokine (C-X-C motif) ligand 10 (CXCL10) may be increased.

In addition, the stem cell may be high-density cultured, and at this time, the high density culturing may be performed at a density of 5,000 cells/cm$^2$ to 20,000 cells/cm$^2$.

As described above, in the case of high density culturing, in the stem cell, the expression of prostaglandin D2 synthase (PTGDS), prostaglandin E synthase (PTGES), vascular cell adhesion protein 1 (VCAM1), chemokine (C-X-C motif) receptor type 7 (CXCR7), or UL16 binding protein 1 (ULBP1) may be increased.

The IFN-γ treatment and the high density culturing may be performed before or after treatment with the SOCS expression or activity inhibitor. In addition, the IFN-γ treatment may also be performed before or after the high density culturing, or during the high density culturing.

In addition, the IFN-γ treatment may be performed immediately before or one or two days before transplantation into the body.

Advantageous Effects

According to the present invention, the inhibition of suppressor of cytokine signaling (SOCS) expression or activity can enhance the immunosuppressive ability of a stem cell. Accordingly, the stem cell with an enhanced immunosuppressive ability can be suitable for use as an effective cell therapeutic agent in an autoimmune disease, organ transplantation rejection, or an allergic disease.

MODE FOR CARRYING OUT THE INVENTION

Hereinafter, the present invention will be described in further detail with reference to the following examples. However, these examples are provided only for illustrative purposes and are not intended to limit the scope of the present invention.

Example 1: Experimental Method 1-1. Isolation and Culture of Human Tissue-Derived Mesenchymal Stem Cells The present experiment was approved (IRB 2011-10-134) by the Institutional Review Board (IRB) of the Samsung Medical Center, and all samples were collected with prior consent. The isolation of mesenchymal stem cells was performed using a conventionally known method. The isolated cells were dispensed at a density of 2×10$^3$ cells/cm$^2$ using Dulbecco's Modified Eagle's Medium (DMEM, Invitrogen-Gibco, Rockville, Md.) containing 10% fetal bovine serum (FBS, Invitrogen-Gibco) and 100 U/ml of penicillin/streptomycin (Invitrogen-Gibco), and incubated at 37° C. under 5% CO$_2$.

1-2. siRNA Transfection

MCSs were plated 24 hours before siRNA transfection to obtain 50% confluence on the day of transfection. Cells were transfected with a Lipofectamine 2000 reagent (Gibco-Invitrogen, Rockville, Md.) according to manufacturer's instructions.

Briefly, the cells were treated with a siRNA-Lipofectamine 2000 complex, and incubated in a CO$_2$ incubator at 37° C. for 18 hours. Subsequently, the medium was replaced with a fresh culture medium (low glucose-Dulbecco's Modified Eagle's Medium (DMEM) containing 10% FBS (Invitrogen-Gibco) and 100 U/ml penicillin/streptomycin (Invitrogen-Gibco), and then the transfected cells were further incubated for 0 hour to 24 hours until a target gene was effectively down-regulated. siRNA and scramble siRNA (sc-37007) targeting each of SOCS1 (sc-40996) and SOCS3 (sc-41000) are both purchased from Santa Cruz Biotechnology (Santa Cruz, Calif.).

1-3. shRNA Transfection

To inhibit the expression of SOCS1, adipose tissue-derived mesenchymal stem cells (AT-MSCs) were treated with SOCS1 short hairpin RNA (shRNA) and a red fluorescent protein (RFP)-expressing adenovirus. In particular, a shRNA sequence targeting SOCS1 was cloned into a shuttle vector (pO6A5-U6-mPGK-TagRFP) containing a human U6 promoter and a TagRFP marker gene to construct the expression vector pO6A5-U6-shSOCS1-mPGK-TagRFP, and the U6-shRNA-SV40-pA region of the shuttle vector was transferred into a BAC vector by recombination. The recovered recombinant adenovirus (Ad5-U6-shSOCS1-mPGK-TagRFP) was proliferated in HEK-293 cells, and HP4, which is a protein transduction domain (PTD), was purchased from Peptron Corporation. To transfect the mesenchymal stem cells with adenovirus particles, the adenovirus particles were treated at a multiplicity of infection (MOI) of 100 along with HP4 (100 nM) and incubated in a serum-free medium at room temperature for 30 minutes. Subsequently, the cultured cells were rinsed with PBS and incubated with Ad-RFP-shSOCS1 and the HP4 preparation, and after 2 hours, the cells were rinsed with PBS and incubated in a serum-containing medium. The selected mesenchymal stem cells were identified by florescence observation through a red fluorescent protein (RFP) and western blotting.

1.4. Immunoblotting (Western Blotting)

Cells were washed with cold PBS (Gibco-Invitrogen) and eluted with a protease inhibitor cocktail (Thermo Fisher Scientific, Rockford, Ill., USA) in 300 µl of a cold RIPA buffer [50 mM Tris-HCl containing 1% Triton X-100, 150 mM NaCl, 0.1% sodium dodecyl sulfate (SDS), and 1% sodium dioxycholate, pH 7.5].

The cell eluate was centrifuged at 3,000 g× at 4° C. for 10 minutes. The supernatant was collected, and protein concentration was determined using a BCA protein assay kit (Thermo Fisher Scientific). For electrophoresis, 30 µg of proteins was lysed in a sample buffer (60 mM Tris-HCl containing 14.4 mM beta-mercaptoethanol, 25% glycerol, 2% SDS, and 0.1% bromophenol blue, pH 6.8), boiled for 5 minutes, and then separated on a 10% SDS reducing gel. The separated proteins were transferred onto a polyvinylidene difluoride (PVDF) membrane (Amersham Biosciences, Little Chalfont, Buckinghamshire, UK) using a trans-blot system (Gibco-Invitrogen). The PVDF membrane was blocked with TBS (10 mM Tris-HCl containing 150 mM NaCl, pH 7.5) containing 5% powdered skim milk (BD Sciences, CA, USA) at room temperature for 1 hour and then washed three times with TBS, and incubated with primary antibodies (all antibodies diluted 1:1000) in TBST (10 mM Tris containing 150 mM NaCl and 0.02% Tween-20, pH 7.5) containing 3% powdered skim milk at 4° C. overnight. The next day, the blot was washed three times with TBST, and incubated with HRP-conjugated secondary antibodies (diluted 1:2,000 or 1:5,000) in TBST containing 3% powdered skim milk at room temperature for 1 hour. After washing three times with TBST, the proteins were visualized with an ECL detection system (Amersham Biosciences).

1-5. Immunocytochemistry Staining

Mesenchymal stem cells were treated with 4% formaldehyde, which is a fixing solution, and allowed to react at room temperature for 30 minutes in a light-blocked state, followed by washing three times with PBS. To detect proteins (PTGES, CXCR7) expressed in the cells, the cells were treated with 0.25% Triton X-100 and allowed to react in a light-blocked state at room temperature for 5 minutes to enhance cell permeability. Subsequently, the cells were washed again three times, and treated with a 5% FBS blocking solution to allow a reaction to occur at room temperature for 1 hour, washed again, treated with primary antibodies purchased from Santa Cruz Biotechnology (Santa Cruz, Calif.), and then also allowed to react at room temperature for 1 hour. Next, the cells were rinsed three times again, treated with Alexa Fluor®488-conjugated goat anti-mouse IgG (Invitrogen-Gibco) secondary antibodies to allow a reaction to occur at room temperature for 1 hour, and then cell images were acquired using a Carl Zeiss LSM 700 confocal microscope system (Jena, Germany).

1-6. T-Cell Proliferation Assay (BrdU Incorporation Assay)

MSCs were seeded at a density of $1.25 \times 10^4$ cells/ml in high glucose DMEM supplemented with 10% FBS in a 96-well plate. After 24 hours, 10 µg/ml of mitomycin-C (Sigma-Aldrich) was added to inhibit cell proliferation. The treated cells were incubated at 37° C. for additional 2 hours, and then rinsed five times with a culture medium. Subsequently, $1 \times 10^5$ human peripheral blood mononuclear cells (hPBMCs) were separated by gradient centrifugation and added to each well to promote T-cell proliferation with 1 µg/ml of phytohemagglutinin (PHA, Sigma-Aldrich). Thereafter, the PHA-activated hPBMCs were incubated on MSCs with mutually different conditions for 3 to 4 days before 5-bromo-2-deoxyuridine (BrdU) was added. Growth levels were measured after 18 hours using an assay kit available from Roche Applied Science (Mannheim, Germany).

1-7. Graft-Versus-Host Disease (GVHD) Animal Model 8- to 9-week-old NOD/SCID immunodeficient mice (Jackson Laboratories, Bar Harbor, Me.) were subjected to 300 cGy total body irradiation, and after 24 hours, human peripheral blood mononuclear cells were intravenously administered thereto. Specifically, $2 \times 10^7$ human peripheral blood mononuclear cells were administered to each mouse along with $1 \times 10^6$ mesenchymal stem cells. Subsequently, the same number of mesenchymal stem cells were repeatedly administered to each mouse on day 7 of administration.

EXAMPLES

Figure 1A:
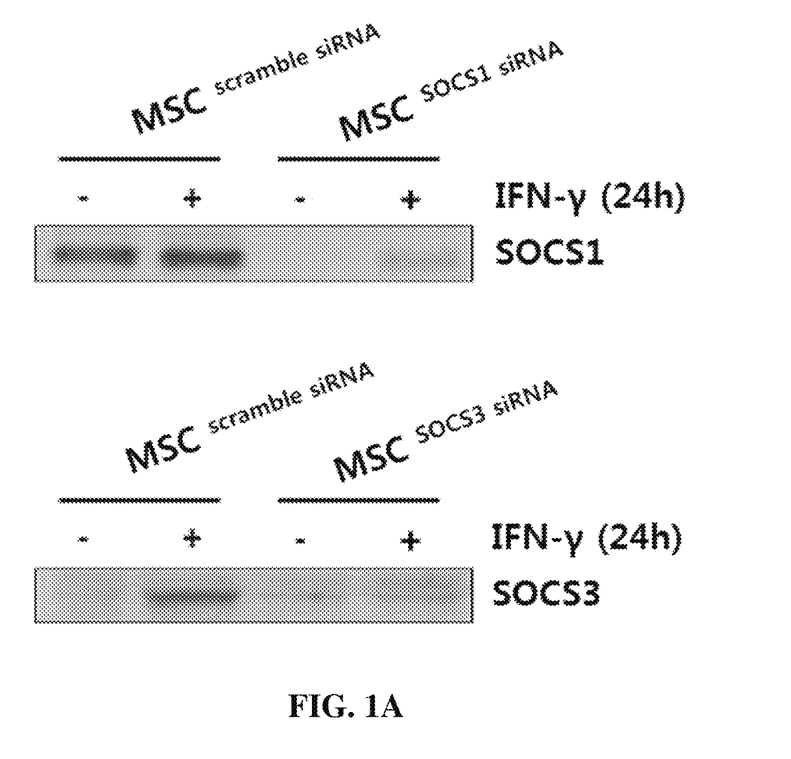
FIG. 1 illustrates in vitro verification results of the immunosuppressive ability of SOCS down-regulated mesenchymal stem cells (MSCs).

Example 1: Evaluation of In Vitro Immunosuppressive Ability of SOCS Down-Regulated MSCs To suppress a SOCS in MSCs, SOCS1 or SOCS3 expression was inhibited using siRNA. As a result, as illustrated in FIG. 1A, it was confirmed that the SOCS1 expression or SOCS3 expression was significantly inhibited in the respective MSCs.

Figure 1B:
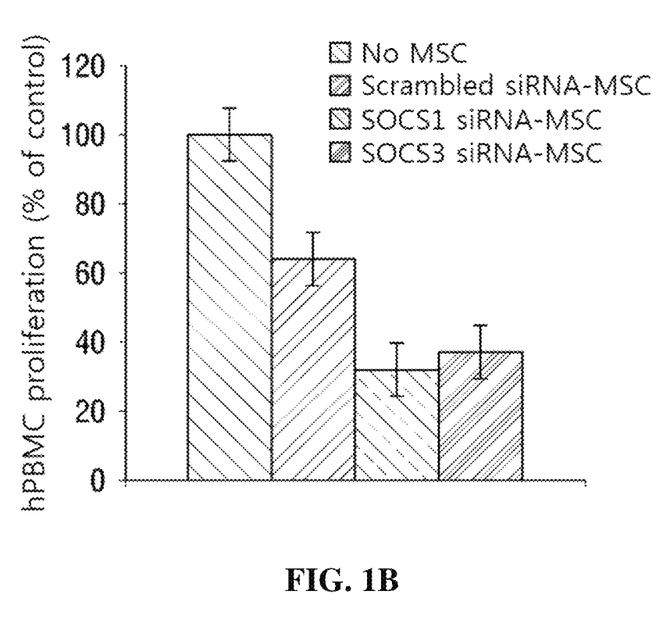

In addition, the SOCS-inhibited MSCs were incubated with PHA-induced hPBMCs, and the proliferative activity thereof was confirmed through the percentage of BrdU+ cells. As a result, as illustrated in FIG. 1B, it was confirmed that SOCS1 siRNA- or SOCS3 siRNA-treated MSCs significantly inhibited the cell proliferation of hPBMCs.

Figure 2A:
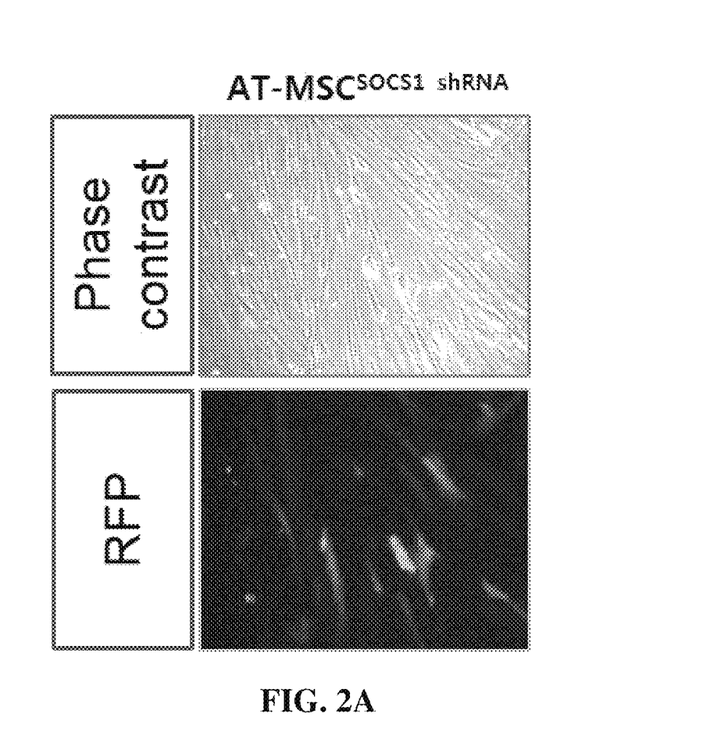
FIG. 2 illustrates red fluorescent staining results (A) and western blotting results (B) of verifying that the expression of the SOCS protein was inhibited in MSCs treated with shRNA targeting a SOCS.
Figure 2B:
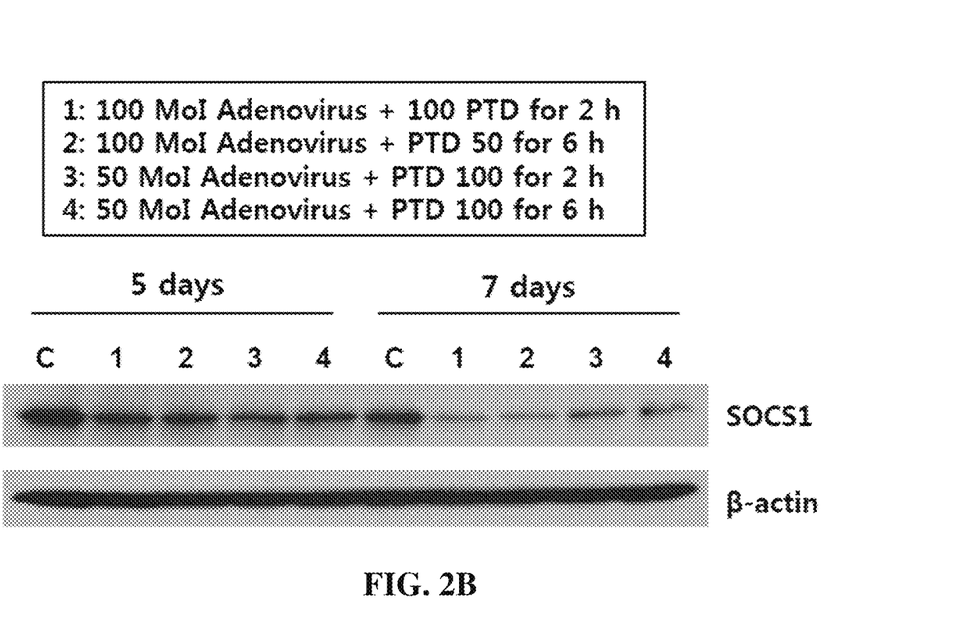

Example 2: Evaluation of In Vivo Immunosuppressive Ability of SOCS Down-Regulated MSCs A shRNA-expressing adenovirus targeting SOCS1 was transduced into adipose tissue-derived mesenchymal stem cells (AT-MSCs) to identify the inhibition of SOCS expression in the MSCs. As a result, as illustrated in FIG. 2, from red fluorescent protein (RFP) labeling results (A) and western blotting results (B), it was confirmed that the expression of the SOCS1 protein in the MSCs was significantly inhibited.

Figure 3:
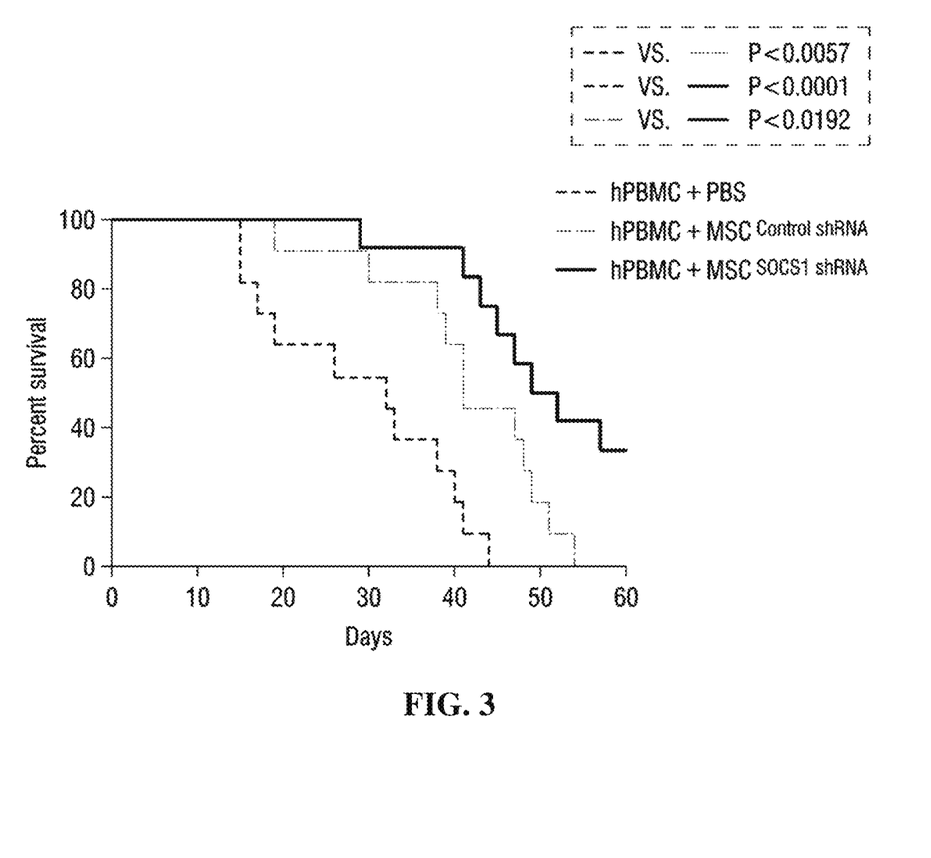
FIG. 3 illustrates verification results of the immunosuppressive ability of SOCS down-regulated MSCs in an in vivo graft-versus-host disease animal model.

In addition, it was examined whether the obtained SOCS down-regulated MSCs exhibited an immunosuppressive ability in an actual graft-versus-host disease (GVHD) animal model. As a result, as illustrated in FIG. 3, it was confirmed that a group treated with MSCs (red line) in which the SOCS had been down-regulated by shRNA significantly increased a survival rate (immunosuppressive ability) compared to a control.

Example 3: Expression Level of SOCS in IFN-γ-Treated MSCs

To enhance an immunosuppressive ability, MSCs were treated with IFN-γ, and then the expression of a suppressor of cytokine signaling (SOCS) was analyzed by immunoblotting.

Figure 4:
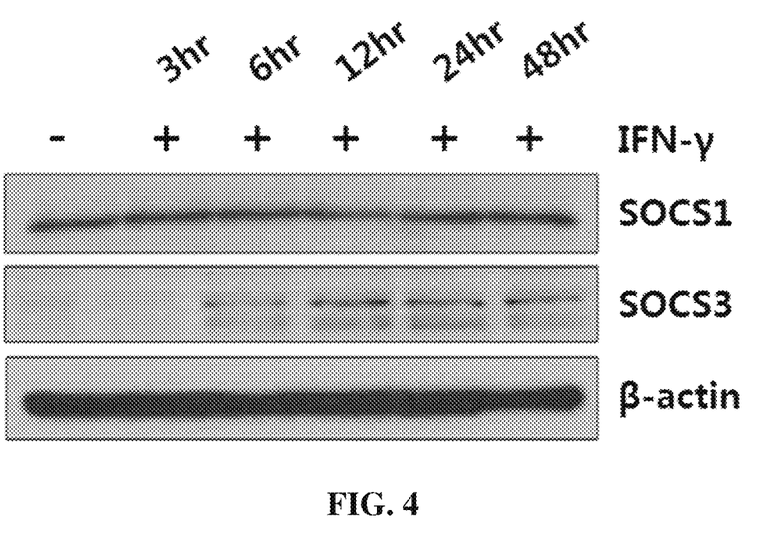
FIG. 4 illustrates verification results of SOCS expression levels in IFN-γ-treated MSCs.

As a result, as illustrated in FIG. 4, it was confirmed that the expression of SOCS (SOCS1 and SOCS3), which is known to regulate a cytokine signal such as IFN-γ, was changed with time. This means that the expression of a SOCS is changed to regulate the signal by IFN-γ.

Example 4: Evaluation of Immunosuppressive Ability Upon Treatment of SOCS Down-Regulated MSCs with IFN-γ

The immunosuppressive ability of the SOCS down-regulated MSCs obtained in Example 2 was evaluated by comparison with the immunosuppressive ability of the SOCS down-regulated MSCs further treated with IFN-γ in an in vivo graft-versus-host disease (GVHD) animal model.

Figure 5:
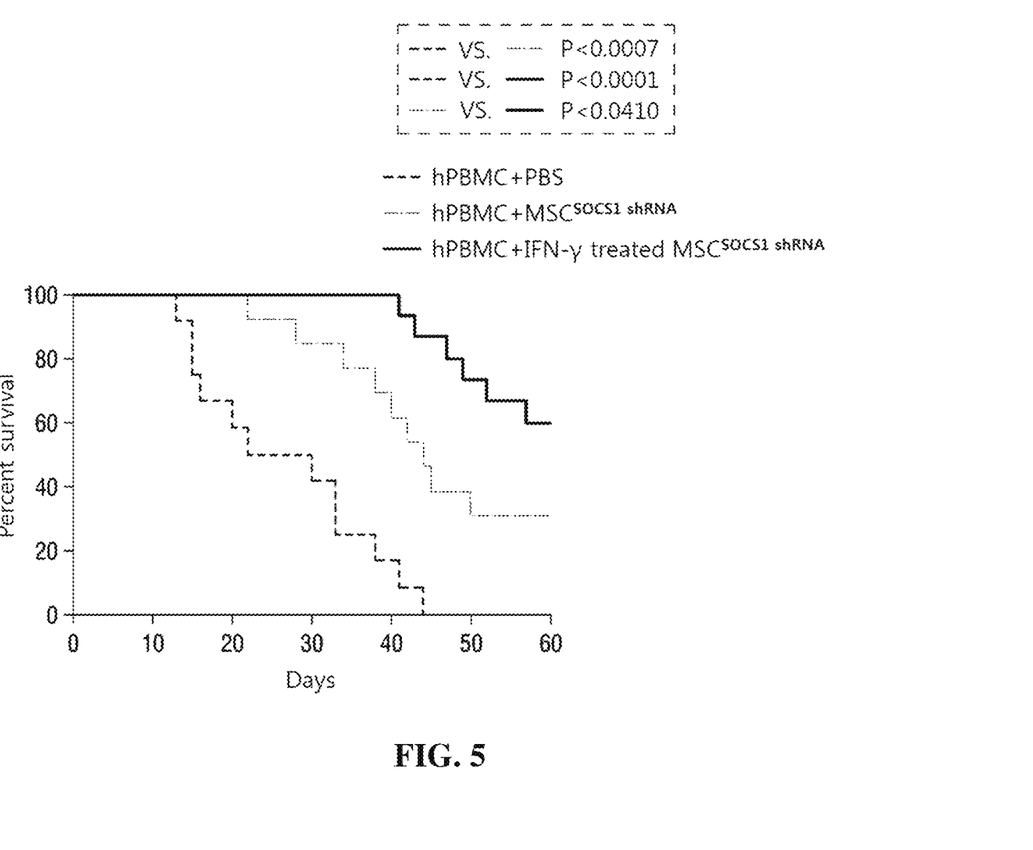
FIG. 5 illustrates comparative evaluation results of a difference in immunosuppressive ability between SOCS down-regulated MSCs and the SOCS down-regulated MSCs further treated with IFN-γ in an in vivo graft-versus-host disease (GVHD) animal model.

As a result, as illustrated in FIG. 5, it was confirmed that, when compared to the MSC-treated group (blue line) in which the SOCS had been down-regulated by shRNA, the SOCS down-regulated MSC-treated group (red line) further treated with IFN-γ significantly increased a survival rate (immunosuppressive ability).

Example 5: Verification of Increase in Immunosuppressive Gene Expression in High-Density Cultured MSCs It was evaluated whether the immunosuppressive ability was further enhanced by high density culturing by confirming an increase in the expression of the prostaglandin E synthase (PTGES) and chemokine (C-X-C motif) receptor type 7 (CXCR7) genes when MSCs were high-density cultured (5,000 cells/cm$^2$).

5.1. Verification of Increase in PTGES Expression

Figure 6A:
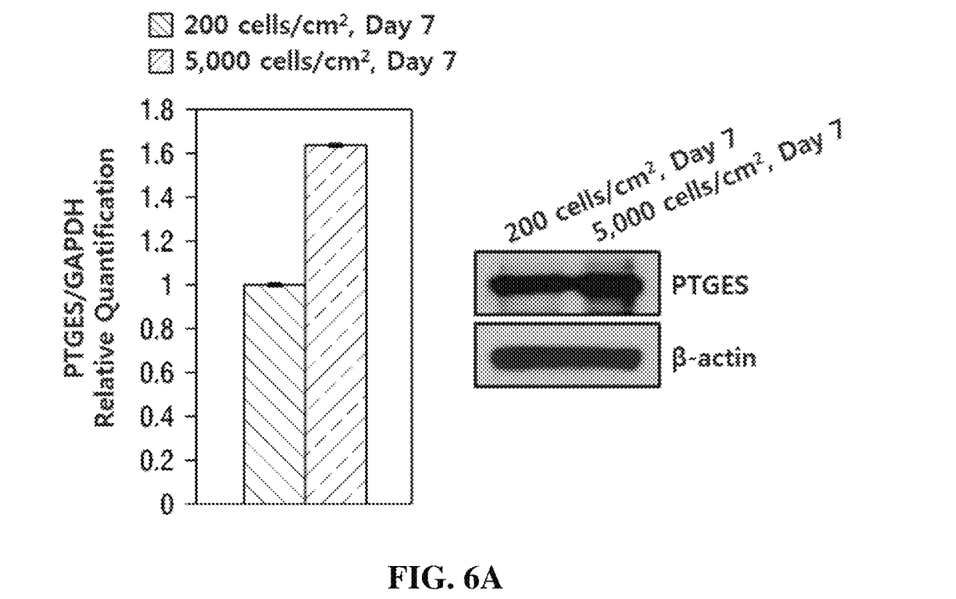
FIG. 6 illustrates verification results of an increase in the expression of PTGES, which is an immunosuppressive marker gene, when MSCs were high-density cultured.
Figure 6B:
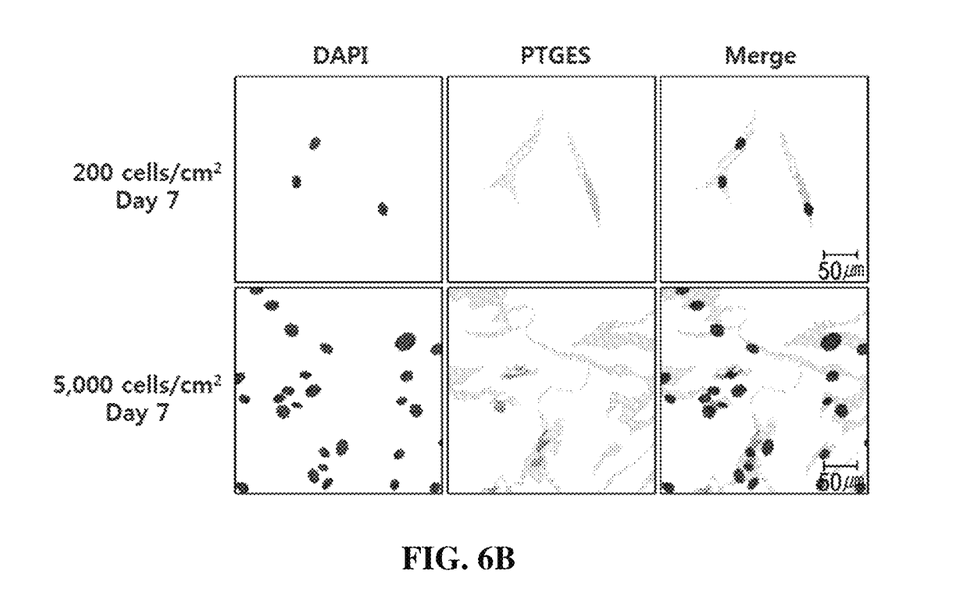

As a result of performing western blotting (A) and immunocytochemistry staining (B) using antibodies specific to PTGES, as illustrated in FIG. 6, it was confirmed that the expression of the PTGES protein was significantly increased during high density culturing (5,000 cells/cm$^2$) compared to low density culturing (200 cells/cm$^2$).

5-2. Verification of Increase in CXCR7 Expression

Figure 7A:
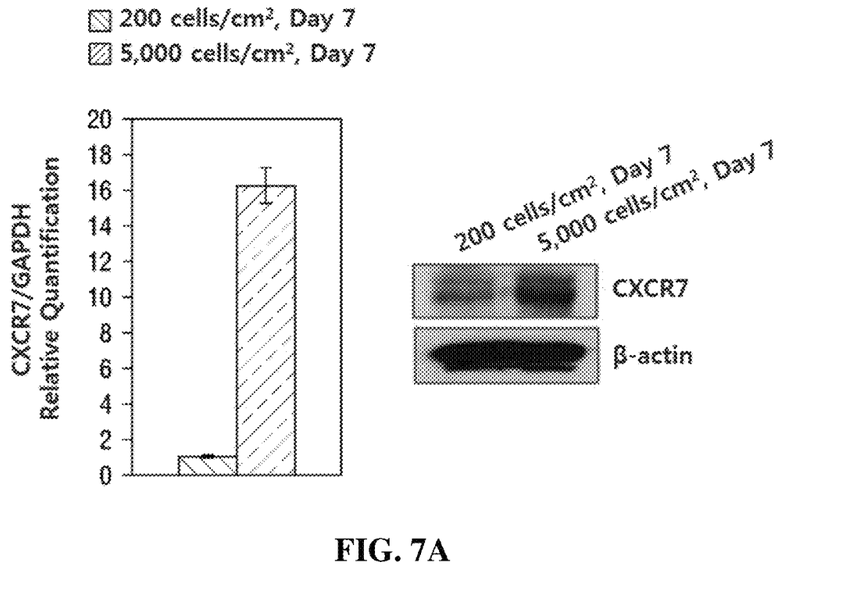
FIG. 7 illustrates verification results of an increase in the expression of CXCR7, which is an immunosuppressive marker gene, when MSCs were high-density cultured.
Figure 7B:
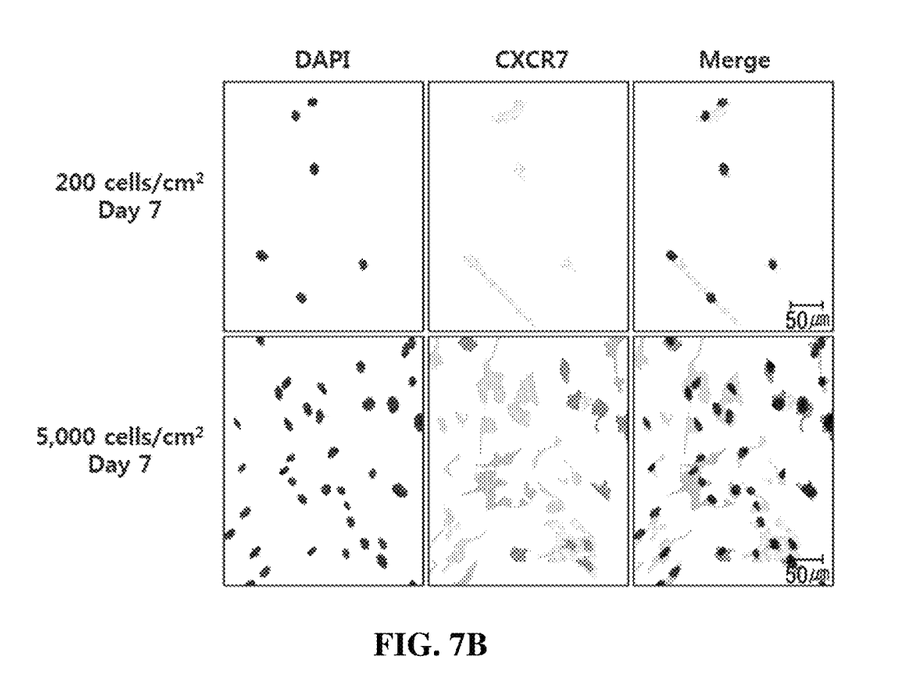

As a result of performing western blotting (A) and immunocytochemistry staining (B) using antibodies specific to CXCR7, as illustrated in FIG. 7, it was confirmed that the expression of the CXCR7 protein was significantly increased during high density culturing (5,000 cells/cm$^2$) compared to low density culturing (200 cells/cm$^2$).

What is claimed is:

1. A method for inducing the immunosuppressive activity of an isolated stem cell, the method comprising:
    a) treating an isolated stem cell with a suppressor of cytokine signaling (SOCS) expression or an inhibitor of SOCS activity; and
    b) culturing the stem cell at a density of about 5,000 cells/cm$^2$, wherein SOCS is down-regulated and the stem cell survival rate is increased compared to a control stem cell.

2. The method of claim 1, wherein the suppressor of cytokine signaling (SOCS) expression or activity inhibitor is selected from the group consisting of small interfering RNA (siRNA), short hairpin RNA (shRNA), microRNA (miRNA), ribozymes, DNAzymes, peptide nucleic acids (PNAs), an antisense oligonucleotide, an antibody, an aptamer, an antagonist, an extract, and a compound that are specific to the suppressor of cytokine signaling (SOCS) or a gene encoding the SOCS.

3. The method of claim 1, further comprising treating the stem cell with interferon gamma.

4. The method of claim 1, wherein the stem cell is derived from an autologous, xenogenic, or allogenic origin.

* * * * *